United States Patent
Iske

(10) Patent No.: US 10,590,678 B2
(45) Date of Patent: Mar. 17, 2020

(54) LOCKING STATE DETECTION APPARATUS

(71) Applicant: B. BRAUN AVITUM AG, Melsungen (DE)

(72) Inventor: Andreas Iske, Soehrewald (DE)

(73) Assignee: B. Braun Avitum AG (DE)

( * ) Notice: Subject to any disclaimer, the term of this patent is extended or adjusted under 35 U.S.C. 154(b) by 439 days.

(21) Appl. No.: 15/286,113

(22) Filed: Oct. 5, 2016

(65) Prior Publication Data

US 2017/0101806 A1    Apr. 13, 2017

(30) Foreign Application Priority Data

Oct. 7, 2015  (DE) .................. 10 2015 117 095

(51) Int. Cl.
  *E05B 39/00*  (2006.01)
  *A61M 1/14*  (2006.01)
  (Continued)

(52) U.S. Cl.
  CPC .............. *E05B 39/00* (2013.01); *A61M 1/14* (2013.01); *A61M 1/1621* (2014.02); *E05B 47/00* (2013.01); *E05C 3/042* (2013.01); *A61M 2205/15* (2013.01); *A61M 2209/08* (2013.01); *E05B 2047/0068* (2013.01); *E05B 2047/0069* (2013.01)

(58) Field of Classification Search
  None
  See application file for complete search history.

(56) References Cited

U.S. PATENT DOCUMENTS 2,708,074 A * 5/1955 Hoskins ................. A61L 11/00
                                                       241/17
6,629,955 B2   10/2003 Morris et al.
(Continued)

FOREIGN PATENT DOCUMENTS

CN       1507359 A      6/2004
CN       1816438 A      8/2006
(Continued)

OTHER PUBLICATIONS

German Search Report, with translation, for DE 10 2015 117 095.7 dated Aug. 4, 2016.
(Continued)

*Primary Examiner* — Richard C Gurtowski
(74) *Attorney, Agent, or Firm* — RatnerPrestia

(57) ABSTRACT

A locking state detector comprises a magnet disposed at a first portion of a casing which has an opening that is lockable with an opening locking means. A detector is disposed at a second portion of the casing, the second portion being spaced apart from the first portion such that a clearance between the first and second portions is formed. An interfering component is fixed to an interfering component pivoting means, which is disposed in the opening locking means and arranged to pivot into the clearance and out of the clearance when the interfering component pivoting means is rotated. The detector is arranged to detect a locked state and a non-locked state of the opening locking means in cooperation with the magnet and the interfering component, and to indicate the detected state for subsequent processing.

17 Claims, 2 Drawing Sheets

(51) Int. Cl.
  *E05C 3/04* (2006.01)
  *A61M 1/16* (2006.01)
  *E05B 47/00* (2006.01)

(56) References Cited

U.S. PATENT DOCUMENTS

| | | |
|---|---|---|
| 7,779,880 B2 | 8/2010 | Sano et al. |
| 8,197,439 B2 | 6/2012 | Wang et al. |
| 10,172,988 B2 | 1/2019 | McGill et al. |
| 2002/0165503 A1 | 11/2002 | Morris et al. |
| 2002/0179622 A1* | 12/2002 | Mase .................. E05B 19/0005 221/9 |
| 2004/0181116 A1* | 9/2004 | Kent .................... A61K 9/5094 600/9 |
| 2006/0144525 A1* | 7/2006 | Sano .................. B29C 65/2046 156/503 |
| 2006/0195064 A1 | 8/2006 | Plahey et al. |
| 2007/0024442 A1 | 2/2007 | Jolley et al. |
| 2007/0199501 A1 | 8/2007 | Gerner |

FOREIGN PATENT DOCUMENTS

| | | |
|---|---|---|
| CN | 101977642 A | 2/2011 |
| CN | 104800903 A | 7/2015 |
| DE | 92 13 595 | 10/1992 |
| DE | 20 2005 013065 | 1/2007 |
| DE | 10 2006 046 086 | 4/2008 |
| DE | 10 2009 012 933 | 9/2010 |
| DE | 10 2009 022838 | 12/2010 |
| DE | 10 2012 111 342 | 5/2014 |
| EP | 2773395 B1 | 9/2014 |
| WO | WO 2012/054942 | 5/2012 |
| WO | WO 2013/67359 | 5/2013 |

OTHER PUBLICATIONS

European Search Report, with translation, for EP 16192615 dated Feb. 2, 2017.
Chinese Office Action for Chinese Application No. 201610875535.2, dated Nov. 28, 2018, with translation, 21 pages.

* cited by examiner

LOCKING STATE DETECTION APPARATUS

CROSS REFERENCE TO RELATED APPLICATIONS

This application claims priority to German application DE 10 2015 117 095.7 filed Oct. 7, 2015, the contents of such application being incorporated by reference herein.

FIELD OF THE INVENTION

The invention relates to a locking state detection apparatus, and in particular to a locking state detection apparatus in the form of a locking apparatus for doors or lids having a lock bar recognition device/sensor for prevailing use with blood treatment devices such as dialysis machines.

BACKGROUND OF THE INVENTION

In for example extracorporeal blood treatment devices, such as dialysis machines for performing a hemodialysis treatment, the dialysis fluid filters which are typically provided for devices of such type are protected by a device door for protection against burns of a user upon touching and for detecting and/or containing leakages.

Machines comprising detection means for recognizing a closed door are known. Thereby and generally, a switching component is movably mounted to for example a door, and a further switching component is, as a fixed counterpart, mounted to for example a casing.

DESCRIPTION OF THE RELATED ART

WO 2013 67359 A2 for example discloses a movable magnet mounted to a hook-like device at a door and a sensor fixedly arranged at a casing for detection of the magnet magnetic field, when the magnet moves toward the sensor. Due to the kind of the described detection using hall effect sensors, which are necessary for a required switching precision, the magnetic field of the magnet can switch the sensor already when the magnet approaches in an opened state. Hall effect sensors are expensive and complex in use, they require a power, supply, and the circuit configuration as a whole is susceptible to temperature changes.

Further, US 2002 0 165 503 A1 shows an arrangement operating with a hook and requiring a sender and a receiver as electronic components. Due to aging or staining, for example, an also required reflection surface for the sensor system of the hook can lose its reflection capacity over time, which is accompanied by a limitation or even loss of its functionality. Furthermore, the deployed components as well require a power supply, a very precise adjustment is necessary, and the arrangement is susceptible to light in itself.

As described above using two prior art examples, known arrangements do recognize closed doors or lids. However, due to switching hysteresis of the sensors used, doors that are not fully closed are not always recognized. Such not fully closed doors then stay ajar. However, the device nevertheless and by mistake recognizes a closed door. Security functions, such as leakage recognition and liquid loss recognition, respectively, may then be inoperable. In addition, the known arrangements partially use elaborate circuitry (hall effect sensor) in order to achieve higher accuracy. However, the elaborate circuitry requires a power supply and is also very susceptible to temperature. Other circuits on the other hand require an active sender and an active receiver. Frequently, also micro switches are employed. These are disadvantageous in that the mechanical components always need to be protected against humidity. Besides, the membranes of the micro switches frequently rip over time which results in a shortfall of the switch.

Hitherto, known recognition devices or recognition systems however do not recognize whether a closed door is actually locked, or is, for example, only left ajar. Doors that are only left ajar may, for example, suspend device protective schemes such as a leakage monitoring. In other words, known devices and systems, in particular in the field of blood treatments, do not yet recognize the actual state of an interlocking device or means.

SUMMARY OF THE INVENTION

An object of the invention therefore resides in providing a locking state recognition apparatus and a locking apparatus having a lock bar recognition, respectively, which provide for safe detection of an actually locked state of a door or lip of a casing, in particular in a blood treatment apparatus.

In accordance with the invention, this object is accomplished with the features defined in the independent claim. Advantageous further developments of the invention are subject of the accompanying dependent claims.

According to a general idea of the invention, for e.g. dialysis liquid filters in blood treatment systems which are configured to improve a quality of the dialysis liquid and which are provided with a casing door for protection of an operator, a user and/or a patient against burns from touching and for recognizing (with a monitoring and for example by a leakage sensor) and containing of leakages, respectively, a door state recognition is provided for that door. In order for the provided protection means to operate safely, the device must be able to recognize whether or not and that, respectively, the casing is closed.

Thereby, according to aspects of the invention, it is not a door which is ajar that is recognized, but it is detected whether and that, respectively, the door is locked, and whether and that, respectively, a provided locking bar is closed as well, i.e. is in a predetermined position so that the protective function of the device is permanently ensured. Further according to aspects of the invention, a partially closed door is recognized, and the device operation is suspended based on such recognition until a complete locking is established. Only a completely locked door allows the operator to operate the device. The recognition is unsusceptible to staining and temperature variations. The configuration of circuitry is simple and does not require any elaborate driver hardware and polling hardware. An accidental unplugging of connectors or a wiring/sensor defect is recognizable as well.

In other words, known solutions only monitor the state of the door via a magnetic sensor or a micro switch. In doing, so, the magnetic sensor or the micro switch may switch too early and misleadingly report a safe state. In contrast thereto, the invention provides a safe recognition of the locking state. A co-operating sensor as a detection device does not only recognize that a door is closed, but also recognizes that a locking bar is closed and locked, respectively, as well. This is only possible when the door of the casing is properly closed and the bar is located in the proper position. Thus, an unsafe state is impossible because it is safely recognized that a door or lid is closed and cannot reopen without being noticed. For this, the position of the locking bar is recognized. The recognition is functional only with, or under, absolutely correct condition of the locking bar.

More specifically, a sensor, which is responsive to a magnet, and the magnet itself are mounted in a casing or housing part. A clearance or air gap is located between these two components. The sensor is kept permanently switched by the magnet. If the casing is closed using a cover and hatch or lid, respectively, the sensor signal output remains unchanged. The signal of the sensor only changes when the locking bar, which as such forms part of the hatch/door and is arranged at the same, respectively, enters into the clearance between the sensor and the magnet. Preferentially, all relevant casing parts are made of a non-ferromagnetic material (e.g. aluminum), and the locking bar is made of a ferromagnetic material.

When the casing/door combination provided with the apparatus according to aspects of the invention is closed, the locking bar safely closes, or locks, the door. In addition, a metal bar latch interrupts a magnetic field. The interruption of the magnetic field results from the bar latch being moved into a clearance between the sensor and the magnet. The bar latch can be made of various materials as long as the material as such has ferromagnetic properties. The magnetic field switches the sensor. In this manner, it is ensured that the door is not only closed, and thus patient and staff are protected against leakages and burns due to hot components, respectively, but also that the door is locked and does not open unwantedly. When the locking bar is not fully closed, the sensor does not change its status, and the device outputs an alarm. When the door is not in the proper end position, the locking bar does not fit into the clearance between the magnet and the sensor. Also in this case, the signal is not changed and influenced, respectively, by the locking bar. It is particularly preferred that the sensor and the magnet are mounted to the same component in a respectively fixed distance from each other. In contrast, the bar latch, acting as an interfering component, is always mounted to another, i.e. different, component.

By way of the locking bar recognition, any access to the secured device can be monitored. Thereby e.g. blood pressure cuffs and/or the like can be accommodated in the device, protected by a lid or hatch, and monitored using a corresponding sensor. An activation of predetermined options can then be carried out via the bar recognition. Instead of configuring a reed sensor/magnet combination, it is also conceivable to configure a hall sensor/magnet combination, which is advantageous in that the switching accuracy can be controlled using such configuration. It is further conceivable to fixedly arrange the interfering component (the bar) on a component and to move, pivot or rotate the unit consisting of the sensor and the magnet toward the interfering component. The clearance into which the interfering component is moved can have various different forms as needed. It is also conceivable to arrange the magnet and the sensor (air) gapless on a same or common side and to configure the interfering component so that it is sufficiently movable toward a so formed magnet-and-sensor unit, in order to thereby sufficiently deviate and/or weaken the magnetic field and to trigger a switchover at the sensor.

More specifically, the object is accomplished by a locking state detector, comprising:

a magnet disposed at a first portion of a casing which has an opening that is lockable with an opening locking means;

a detector disposed at a second portion of the casing, the second portion being spaced apart from the first portion such that a clearance between the first and second portions is formed; and an interfering component which is fixed to an interfering component pivoting means disposed in the opening locking means in a non-pivotable manner and arranged to pivot into the clearance and out of the clearance when the interfering component pivoting means is rotated, wherein the detector is arranged to detect a locked state and a non-locked state of the opening locking means in cooperation with the magnet and the interfering component, and to indicate the state for subsequent processing.

Preferentially, the detector is arranged to detect and to signal a locked state of the opening locking means only when the interfering component is located at a position within the clearance.

Preferentially, the opening locking means is a device door and the detector is configured to perform recognition of a state of this door, wherein a locked state of the door is recognized at a predetermined position of the interfering component and only then the operation of the device is allowed for an operator.

Preferentially, an interruption at connection means, which include at least a connector and/or a wiring connection, is detectable and interpretable as an unlocked state of the opening locking means.

Preferentially, the magnet and the detector are fixedly arranged.

Preferentially, the magnet and the detector are in operative connection such that the detector forms a sensor configured to be permanently switched by the magnet and to change its signal output only when the interfering component moves into the clearance and interrupts or at least weakens the magnetic field of the magnet.

Preferentially, casing-side peripheral components including all casing parts are made of a non-ferromagnetic material.

Preferentially, casing-side peripheral components including all casing parts are made of aluminum and/or plastic material.

Preferentially, the interfering component is made of a ferromagnetic material.

Preferentially, the magnet and the detector are respectively arranged at a first component or portion in a fixed distance from each other, and the interfering component is arranged at a second component or portion which is different from the first component or portion.

Preferentially, the detector and the magnet form a reed sensor/magnet combination.

Alternatively preferred, the detector and the magnet form a hall effect sensor/magnet combination.

Preferentially, the interfering component is fixedly arranged at a component or portion, and a unit including the detector and the magnet is movable, pivotable and/or rotatable to the interfering component.

Preferentially, the magnet and the detector are disposed facing each other, and an air gap of a predetermined width is formed between them as the clearance, the predetermined width allowing a movement of the interfering component into and out of the gap.

Alternatively preferred, the magnet and the detector are disposed at a same side and spaced from one another, and the clearance is formed between them, along which the interfering component is approachable such that a deviation and/or weakening of the magnetic field of the magnet occurs that triggers a switchover of the detector.

Preferentially, an extracorporeal blood treatment apparatus can comprise a locking state detector of the aforementioned kind.

Preferentially, such an extracorporeal blood treatment apparatus is configured as a dialysis machine having at least one dialysis liquid filter and at least one leakage sensor as a means for monitoring the at least one dialysis liquid filter.

BRIEF DESCRIPTION OF THE DRAWING

The invention is best understood from the following detailed description when read in connection with the accompanying drawing. Included in the drawing is the following figure.

DETAILED DESCRIPTION OF THE PREFERRED EMBODIMENTS

Figure 1:
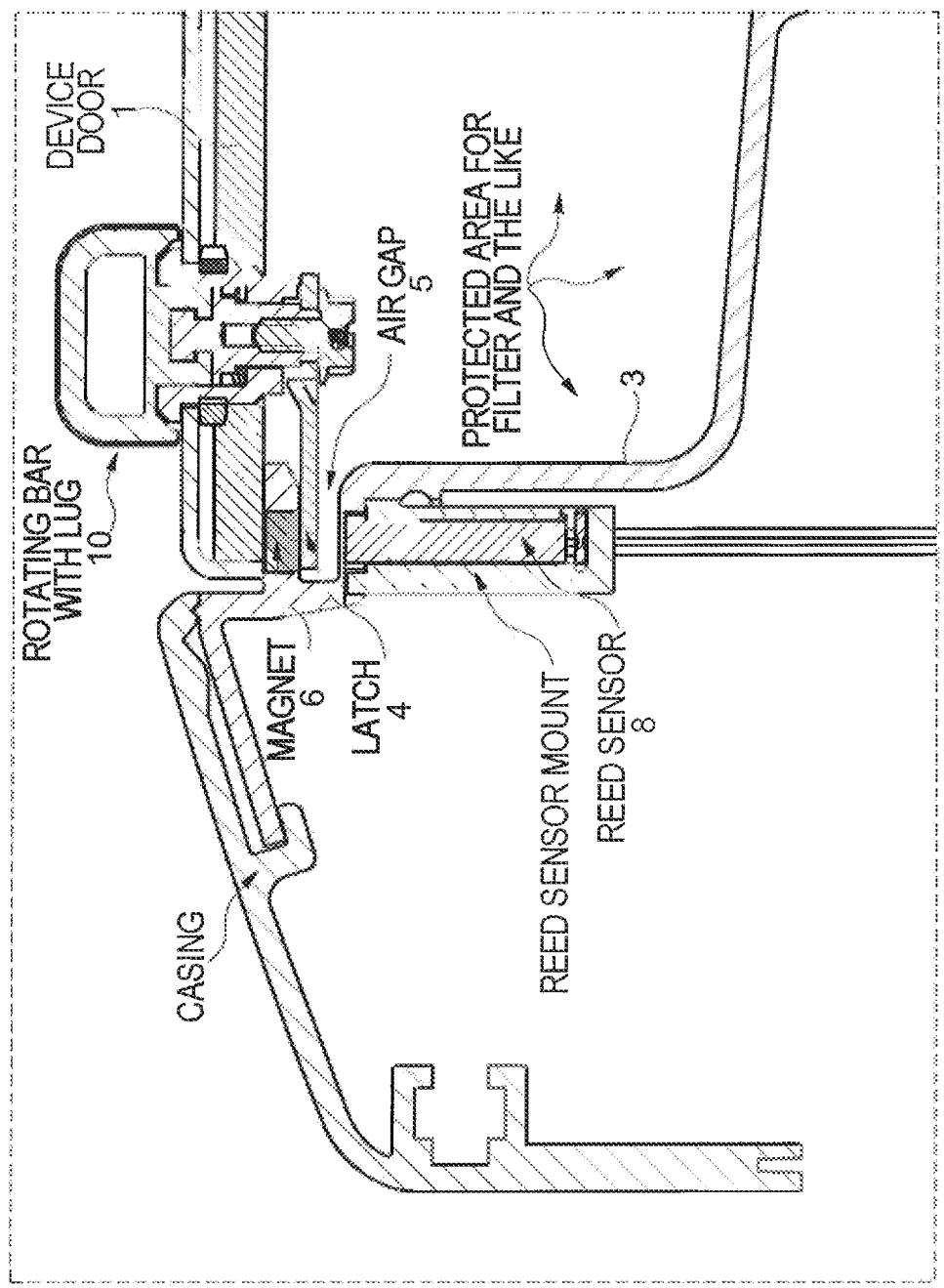
FIG. 1 schematically, partially and in a simplified manner shows a sectional view illustrating a locking state detector apparatus for a door or a lid having a locking bar recognition according to an embodiment.

It is noted that like reference numerals in the figures respectively designate the same elements, and that elements being repeatedly depicted equally are of substantial equivalent nature and insofar not always provided with reference signs. A single element may stand representatively for plural identically illustrated elements.

FIG. 1 schematically, partially and in a simplified manner shows a sectional view illustrating a locking state detector apparatus in conjunction with a locking apparatus including a locking bar recognition for a door or a lid covering or closing, respectively, an opening of a device according to an embodiment.

Figure 2:
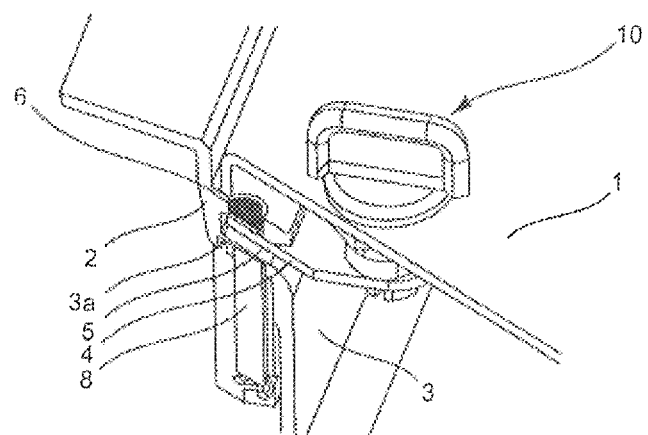
FIG. 2 schematically shows a partial perspective view of the locking state detector apparatus of FIG. 1 in a mounted state.

The locking state detector apparatus, which is shown in a sectional view in FIG. 1 and a perspective view in FIG. 2, comprises a magnet 6 as a magnetic means. The magnet 6 is disposed on or at a first portion 2 of a casing of e.g. a blood treatment apparatus, such as a dialysis machine, having an opening which can be closed with a door 1 (or a lid or hatch) as an opening closing device. On or at a second portion 3 of the casing, a sensor 8 is disposed as a detector which is positionally spaced from the first portion such that a clearance 5, which is an air gap in FIG. 1, is formed between the first portion and the second portion. In order to be protected against wear, the sensor 8 can be covered by a projection of wall 3 of the casing, i.e. does not have to be within the clearance 5 and the air gap, respectively, with a front side thereof. An interfering component, which is a bar or locking bar 4 in this embodiment, is fixedly mounted, i.e. cannot rotate, to a closing or, locking mechanism 10 forming an interfering component pivoting means, and arranged to move or pivot into the clearance 5 and out of the clearance 5, for example clockwise/counter-clockwise, when the locking mechanism 10 is rotated. The sensor 8 is in co-operation with the magnet 6 and its magnetic field, respectively, and the bar 4, as the interfering component which influences (weakens, deviates and/or interrupts) the magnetic field, arranged to detect a locked state and an unlocked state of the door 1 and to signal the detected state toward a downstream hardware and/or software for subsequent processing.

In other words, the magnet 6 and the sensor 8 are each disposed on or at a first (casing) element or portion in a predetermined fixed distance from each other, and the rotatable bar 4 is disposed on or at a second element or portion, in this embodiment the door 1, which insofar differs from the first element or portion which is attributable to the casing.

In the present embodiment, the sensor 8 is arranged to detect and to signal a locked state of the door 1 only when the bar 4 is located in a position pivoted into the clearance 5 i.e. the sensor 8 is configured to perform a casing door state recognition, wherein an actually locked state of the casing door is recognized in a predetermined position of the interfering component, and only then the operation of the device is allowed for an operator. In other words, the sensor 8 does not only recognize whether or that, respectively, the door 1 is closed, but in addition that it is properly locked, and releases the device operation only when the locked state is present, with its output signal corresponding to that state.

In the present context, the interconnection of the sensor 8 is configured such that its output signal upon e.g. an interruption at connection means, which at least include a connector and/or a cable connection, also corresponds to the non-locked or unlocked state so that a malfunction or an error of this kind is detectable and interpretable as an unlocked state of the door (followed by a suspension of the device operation).

In the example shown in FIG. 1, the magnet 6 and the sensor 8 are arranged stationary, i.e. fixedly mounted to respective casing parts or casing portions, and thereby are in co-operation with each other such that the sensor 8 is kept permanently switched, or activated, by the magnet 6 and the magnetic field thereof, respectively, and changes its signal output only when the bar 4 pivots into the clearance 5 and thereby interrupts or at least weakens the magnetic field.

In the present embodiment, this works particularly well if surrounding casing-side components (for example all casing parts) consist of a non-ferromagnetic material, such as e.g. aluminum, and the bar 4 consists of a ferromagnetic material.

In this case, the sensor 8 and the magnet 6 form a reed sensor/magnet-combination, or pair, that operates according to the reed contact principle. Alternatively, the sensor 8 and the magnet 6 may form a hall effect sensor/magnet combination, or pair, which further advantageously allows for adaptation or setting and adjustment, respectively, and thus improvement of the switching accuracy.

In an alternative and not illustrated modification, the bar 4 may be disposed fixedly on or at a predetermined element or portion, and the sensor 8 and the magnet 6 may be disposed on or at a unit which is movable, pivotable and/or rotatable toward or to the interfering component. In other words, for example the bar 4 or a latch type element may be mounted fixedly on or to casing portion 2 or 3, and a unit or subassembly consisting of the sensor 8 and the magnet 6 in predetermined positional relationship may be mounted on or to the locking apparatus 10 and upon rotation thereof pivoted to the fixedly mounted bar 4 in such a manner that it comes to rest in the clearance 5 and air gap, respectively, of the sensor-magnet-arrangement. It is noted that for the event of an air gap the magnet 6 and the sensor 8 are disposed facing each other and the air gap is formed between them as the clearance 5 of a predetermined width that allows the bar 4 to pivot in and out.

Alternatively, the magnet 6 and the sensor 8 may be arranged spaced apart from each other on one and the same, i.e. an equal, side. In this case, the clearance 5 is formed between them, and the bar 4 can be advanced along the clearance 5 toward the sensor 8 and the magnet 6 in such a manner that a deflection and/or weakening of the magnetic field of the magnet 6 is effectuated which triggers a switchover of the sensor 8.

A particularly advantageous area of application of the present embodiment resides in an extracorporeal blood treatment apparatus which includes a locking state detection apparatus as described above. In particular, such a blood treatment apparatus may be a dialysis device or machine with at least one dialysis liquid filter and at least one leakage sensor as one of devices for monitoring the at least one dialysis liquid filter.

The invention is, however, not limited to extracorporeal blood treatment apparatus, but is particularly in the medical field applicable where a safe locking of a door or lid has to be ensured and a not safely locked door or lid shall for safety reasons lead to a forced shutdown or forced closing down of a device or an apparatus and a corresponding system or facility, respectively, including the door or lid to be monitored.

The invention thus advantageously achieves a safe recognition of an opening action of a door or a non-properly closed or locked door with a sensor 8. The relevant apparatus parts including downstream processing (hardware and software) are independent of the environmental temperature, because the sensor 8 switches between two defined states which can safely be reached also under changing environmental temperatures. A degradation of the operation due to staining is impossible because of the contactless switching operation and because a positioning on or at the device is possible in a protected manner. Both the magnet 6 and the sensor 8 can be accommodated and mounted maintenance-free and stationary in an element, component or casing. All elements and components including the casing can be made and produced from all non-ferromagnetic materials including plastic materials and/or aluminum. No additional power supply is required for the locking state detector apparatus, and the entire assembly is free from being affected by environmental light. Expensive and sensitive components such as a sender and/or a receiver are not necessary. Besides, a cable break or a non-plugged connector is recognized by the device, which can then immediately establish the safe state.

All in all, the circuitry according to aspects of the invention provides for recognition of a locked door and can prevent that an accidental opening operation goes unnoticed. In addition, the proposed solution is safe in execution, i.e. the system is not affected by deviations of the magnetic fields caused by production and varying switching hysteresis of the sensor 8, respectively. Also, the system cannot be affected by external disturbances (staining, temperature changes, varying light conditions, wear and the like).

As described above, a locking state detector apparatus comprises a magnet device 6 (a magnet in the above embodiment) disposed at a first portion 2 of a casing which has an opening that is lockable with an opening locking means 1 (a door, hatch or lid in the above embodiment). A detector device 8 (a sensor in the above embodiment) is disposed at a second portion 3 of the casing, the second portion being spaced apart from the first portion 2 such that a clearance 5 between the first and second portions 2, 3 is formed. An interfering component 4 (a pivotable bar in the above embodiment) which is fixed to an interfering component pivoting means 10 (an arrangement with which the bar 4 can e.g. be moved to and fro between predetermined positions in the above embodiment) is disposed in the opening locking means in a non-pivotable manner and arranged to pivot into the clearance 5 and out of the clearance 5 when the interfering component pivoting means 10 is rotated. The detector device 8 is arranged to detect a locked state and a non-locked state of the opening locking means 1 in co-operation with the magnet 6 and the interfering component 4, and to indicate the state for subsequent processing.

The invention claimed is:

1. An apparatus comprising:
   an extracorporeal blood treatment device having a casing, the casing having an opening;
   an opening locking means configured to lock the opening of the casing;
   a magnet disposed at a first portion of the casing;
   a detector disposed at a second portion of the casing, the second portion being spaced apart from the first portion such that a clearance between the first and second portions is formed; and
   an interfering component fixed to an interfering component pivoting means disposed in the opening locking means and arranged to pivot into the clearance and out of the clearance when the interfering component pivoting means is rotated;
   wherein the detector is arranged to detect a locked state and a non-locked state of the opening locking means in cooperation with the magnet and the interfering component, to indicate the detected state for subsequent processing, and to detect and signal the locked state of the opening locking means, and
   wherein the extracorporeal blood treatment device is configured to operate only in the locked state of the opening locking means.

2. An apparatus as defined in claim 1, wherein the detector is arranged to detect and to signal the locked state of the opening locking means only when the interfering component is located at a position within the clearance.

3. An apparatus as defined in claim 1, wherein the opening locking means is a door or lid and the detector is configured to perform a recognition of a state of this door or lid, wherein the detector recognizes the locked state of the door or lid at a predetermined position of the interfering component and wherein the extracorporeal blood treatment device is configured for operating by an operator only in the locked state of the door or lid.

4. An apparatus as defined in claim 1, wherein an interruption at a connection means for the detector is detectable and interpretable as an unlocked state of the opening locking means.

5. An apparatus as defined in claim 4, wherein the connection means includes a connector and/or a wiring connection.

6. An apparatus as defined in claim 1, wherein the magnet and the detector are fixedly arranged.

7. An apparatus as defined in claim 1, wherein the magnet and the detector are in operative connection such that the detector forms a sensor configured to be permanently switched by the magnet and to change its signal output only when the interfering component moves into the clearance and interrupts or at least weakens the magnetic field of the magnet.

8. An apparatus as defined in claim 1, wherein casing-side peripheral components including all casing parts are made of a non-ferromagnetic material.

9. An apparatus as defined in claim 1, wherein casing-side peripheral components including all casing parts are made of aluminum and/or plastic material.

10. An apparatus as defined in claim 1, wherein the interfering component is made of a ferromagnetic material.

11. An apparatus as defined in claim 1, wherein the magnet and the detector are respectively arranged at a first component or portion in a fixed distance from each other, and the interfering component is arranged at a second component or portion which is different from the first component or portion.

12. An apparatus as defined in claim 1, wherein the detector and the magnet form a reed sensor/magnet combination.

13. An apparatus as defined in claim 1, wherein the detector and the magnet form a hall effect sensor/magnet combination.

14. An apparatus as defined in claim 1, wherein the interfering component is fixedly arranged at a component or portion, and a unit including the detector and the magnet is movable, pivotable and/or rotatable to the interfering component.

15. An apparatus as defined in claim 1, wherein the magnet and the detector are disposed facing each other, and an air gap of a predetermined width is formed between them as the clearance, the predetermined width allowing a movement of the interfering component into and out of the air gap.

16. An apparatus as defined in claim 1, wherein the magnet and the detector are disposed at a same side of the casing and spaced from one another, and the clearance is formed between them, along which the interfering component is approachable such that a deviation and/or weakening of the magnetic field of the magnet occurs that triggers a switchover of the detector.

17. An apparatus as defined in claim 1, wherein the extracorporeal blood treatment device is configured as a dialysis machine having at least one dialysis liquid filter and at least one leakage sensor as a means for monitoring the at least one dialysis liquid filter.

* * * * *